(12) United States Patent
Wang et al.

(10) Patent No.: US 7,435,847 B2
(45) Date of Patent: Oct. 14, 2008

(54) PREPARATION OF SOLID AMMONIUM GLYPHOSATE USING ORGANIC SOLVENT IN EXTRACTION

(75) Inventors: Wei Wang, Jiande (CN); Bufan Ren, Jiande (CN); Shuguang Zhou, Jiande (CN); Min Bao, Jiande (CN); Hongchao Zheng, Jiande (CN); Baiqing Zhang, Jiande (CN); Jiang Li, Jiande (TW)

(73) Assignee: Zhejiang Xin', Zhejiang Province (CN)

( * ) Notice: Subject to any disclaimer, the term of this patent is extended or adjusted under 35 U.S.C. 154(b) by 606 days.

(21) Appl. No.: 10/521,649

(22) PCT Filed: Sep. 4, 2003

(86) PCT No.: PCT/CN03/00747

§ 371 (c)(1), (2), (4) Date: Jan. 13, 2005

(87) PCT Pub. No.: WO2004/022571

PCT Pub. Date: Mar. 18, 2004

(65) Prior Publication Data

US 2005/0209105 A1    Sep. 22, 2005

(30) Foreign Application Priority Data

Sep. 5, 2002    (CN) ............................... 02 1 41788

(51) Int. Cl.
*C07F 9/38*    (2006.01)
*A01N 57/18*    (2006.01)
*C07F 9/22*    (2006.01)

(52) U.S. Cl. ....................................... 562/17; 504/206

(58) Field of Classification Search ................. 504/100, 504/206; 562/17
See application file for complete search history.

(56) References Cited

FOREIGN PATENT DOCUMENTS

| CN | 1192743 A | 9/1998 |
|---|---|---|
| CN | 1260349 A | 7/2000 |
| CN | 1068008 C | 7/2001 |
| CN | 1340508 A | 3/2002 |
| CN | 1365254 A | 8/2002 |
| CN | 1365255 A | 8/2002 |
| WO | WO 0108492 A1 * | 2/2001 |

* cited by examiner

*Primary Examiner*—Johann Richter
*Assistant Examiner*—Andriae M Holt
(74) *Attorney, Agent, or Firm*—Scully, Scott, Murphy & Presser, P.C.

(57) ABSTRACT

A method of preparing ammonium glyphosate suitable for preparation of water-soluble solid ammonium glyphosate formulation by an extraction with organic solvent in a gas-liquid-solid phase system, which comprises adding glyphosate and water into a reactor with a stirer, introducing ammonia to carry out the reaction, an aqueous solution of ammonium glyphosate is formed after the reaction is completed; adding a water-soluble organic solvent such as methanol and/or ethanol and/or methylal to decrease the solubility of the ammonium glyphosate in the system, thereby crystallizing out ammonium glyphosate; and filtering in suction or further oven-drying to obtain the solid ammonium glyphosate. The organic solvent may be recovered and reused by rectifying or distilling, the remainder residue may be returned to the reaction procedure or used in the preparation of the aqueous formulation of ammonium glyphosate.

12 Claims, 1 Drawing Sheet

PREPARATION OF SOLID AMMONIUM GLYPHOSATE USING ORGANIC SOLVENT IN EXTRACTION

FIELD OF THE INVENTION

The present invention relates to a process for preparing solid ammonium glyphosate, more particularly to a process for preparing solid ammonium glyphosate useful in the preparation of a water-soluble solid formulation of ammonium glyphosate by the reaction in a gas-liquid-solid phase system and the extraction with an organic solvent.

BACKGROUND OF THE INVENTION

The chemical name of glyphosate is N-phosphonomethyl glycine, which has the following molecular formula.

Glyphosate is a broad-spectrum sterile herbicide highly effective in the prevention and control of various malignant deep-rooted weeds due to good systemic conduction performance. Recently, its sales volume is gradually increased. The application field thereof is further extended with the gradual popularization of glyphosate-resisting transgenosis crops. Now, it has become a herbicide with the highest sales volume and the quickest speed increased in its production in the world.

Because the solubility of glyphosate in water is very low (1.2 g per 100 g water at 25° C.), as for practical application, the glyphosate is usually processed into water-soluble salts, and is commercially available as an aqueous formulation of glyphosate isopropylamine salt, an aqueous formulation of glyphosate trimesium, an aqueous formulation or a water-soluble powder (granula) of ammonium (sodium) glyphosate. Because the aqueous formulation of glyphosate salt contains a great amount of water as a solvent and its package has an increased weight and volume, the water-soluble solid formulation has a relatively low cost. As for the end users, the products with lower price and better performance are required. It is obvious that the water-soluble solid formulation of ammonium glyphosate is more competitive than the aqueous formulation thereof.

Chinese Patent Application No. CN-96196134.1, which was published on Sep. 9, 1998 and was issued to Monsanto Company of American on Jul. 18, 2001, shows that great efforts have been made for the preparation and use of compositions of dry glyphosate formulation, and for related methods. Herein, the related patents and references are used as the references for the present invention. The patent discloses a process for preparing ammonium glyphosate by the reaction of an aqueous ammonium hydroxide solution (ammonia water) with glyphosate in a liquid-solid reaction system. Since the concentration of ammonia water is only 29%, namely, it contains a large amount of water, continuous drying is required so as to keep an appropriate water content during the process. Further, the rate for introducing ammonia water is required to control strictly so as to ensure the rate for introducing water into the system less than that for removing it from the system during the reaction. The water content should be periodically measured, and the product should be dried and then pulverized. Furthermore, sodium sulfite as an antioxidant (oxidation inhibitor) is required further to add during the reaction in order to decrease the oxidization of glyphosate by hot air because the oxidation causes formation nitrosamine which content needs to be controlled. Therefore, the technology and control are relatively complicated to some extent, and a large amount of water has to be removed by hot wind, so the energy consumption is higher.

Chinese Patent Application No. CN-96196133.3, which was published on Sep. 9, 1998 and was grant on Jul. 4, 2001, discloses a process for preparing ammonium glyphosate by the reaction of glyphosate and anhydrous ammonia. The process needs to use a "self-cleaning type" of autoclave equipped a "propeller" which has a precision dimension and is able to scrape continuously the products deposited on the reactor wall, otherwise, the solid deposition formed will affect the removal of reaction heat. Furthermore, the rate for introducing ammonia is strictly controlled in order to ensure introducing the ammonia and glyphosate into the reactor in a manner that they are completely homogeneous dispersed. If the inlet for ammonia is not set in an appropriate position, fouling and clogging will easily occur at the inlet and solid aggregations will also be formed. The disadvantages of the process are that it is difficult to removal the reaction heat from the gas-solid reaction system and the reaction rate is slow.

Chinese Patent Application No. CN-99119971.5, which was published on Jul. 19, 2000 and was grant on Oct. 10, 2001, discloses a commercial process for preparing ammonium glyphosate by the reaction of glyphosate with liquid ammonia. Because the process is carried out directly through the liquid-solid reaction of liquid ammonia with glyphosate, it is required to be carried out under a pressure of 1.0-2.8 MPa while the reaction heat is required to remove timely during the reaction to avoid resulting in danger under too high pressure. The process has disadvantages in that the reaction has to be conducted at a higher pressure and bigger equipment is further required to install for recovering ammonia.

Although the aforementioned inventions provide the process for preparing dry ammonium glyphosate salt that can be used in the preparation of the water-soluble solid formulation, the processes suffer from deficiencies such as slow reaction rate, high cost or complicated technology and the like. That is, the prior arts are such unsatisfactory that there is still a need for a further invention. In this regard, the present invention solves the problems associated with the process in the prior arts and meets requirements that are not yet realized in aforementioned inventions or well-know technologies.

DISCLOSURE OF THE PRESENT INVENTION

An object of the present invention is to overcome the deficiencies associated with the process in the prior arts and provide a novel process for preparing ammonium glyphosate that can be used in the preparation of the water-soluble solid formulation by the extraction with an organic solvent.

Another object of the present invention is to provide an easily industrialized process for preparing ammonium glyphosate.

These and other objects of the present invention are further illustrated in detail by the following description.

The present invention provides a process for preparing solid ammonium glyphosate by the reaction in a gas-liquid-solid phase system, which comprises adding glyphosate and water into a normal reactor, introducing ammonia to carry out the reaction, an aqueous solution of ammonium glyphosate is formed after the reaction is completed; adding an organic solvent with a relatively high solubility in water to decrease the solubility of the ammonium glyphosate in the system, thereby crystallizing out ammonium glyphosate, and filtering in suction to obtain the solid ammonium glyphosate. The organic solvent recovered by rectifying or distilling the mother liquor may be reused, the remainder residue may be returned to the reaction procedure or used in the preparation of the aqueous formulation of ammonium glyphosate.

Powder of crystalline ammonium glyphosate is obtained in a simple method by reacting glyphosate with ammonia (or ammonia water) in aqueous phase and adding an organic solvent after the reaction is finished to decrease the solubility of ammonium glyphosate in the system. Therefore, a desired and easily industrialized process is provided for preparing ammonium glyphosate salt that is useful in the preparation of a herbicide composition of water-soluble solid ammonium glyphosate salt.

The ammonium glyphosate is present in a formula as the following:

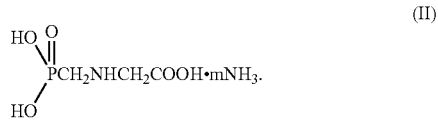

(II)

Wherein m is a positive integer from 1 to 3, the ammonium cation may link to the hydroxyl which is bonded with a carbonyl or a phosphoryl. As for the single molecule, m equals 1-3. The generally used ammonium glyphosate salt is a mono-ammonium salt, namely, m equals 1. However, it may not be deemed simply that the ammonium glyphosate salt obtained in practical production has m just equal to a positive integer, but a value in the range of 0.8-1.3. These substances have very high solubility in water and the concentration of their aqueous solutions may be more than 20% at room temperature. However, they have very low solubility in such organic solvents that are completely miscible with any proportion of water or have a relatively high solubility in water. Thus, after the reaction is ended, such organic solvent(s) is(are) added to the reaction solution to form a homogeneous solution with water in the system, thereby substantially decreasing the solubility of the ammonium glyphosate salt therein and crystallizing the salt out. Such solvents may include, or may be, alcohols and acetals, etc. or a mixture of two or more solvents. The alcohols may include monobase alcohols having 1-4 carbon atoms. It is preferred to use methanol, ethanol, propanol, butanol and methylal in terms of cost effective, which can be used alone or as a mixture of thereof. It is not recommended to use the organic solvent having a lower solubility in water, such as aliphatic hydrocarbon, aromatic hydrocarbon and ethers and the like. Such solvents are not able to form a stable homogeneous phase in water and cannot effectively isolat ammonium glyphosate salt since said salt dissolved in the aqueous layer after phase separation. Certainly, if the organic solvent which is used is mixed with a little amount (for, example, less than 5%) of organic or inorganic substances that are not selected in the present invention, such as, aliphatic hydrocarbon, aromatic hydrocarbon, ethers and the like, there will be no effect on the realization of the process according to the present invention.

Figure 1:
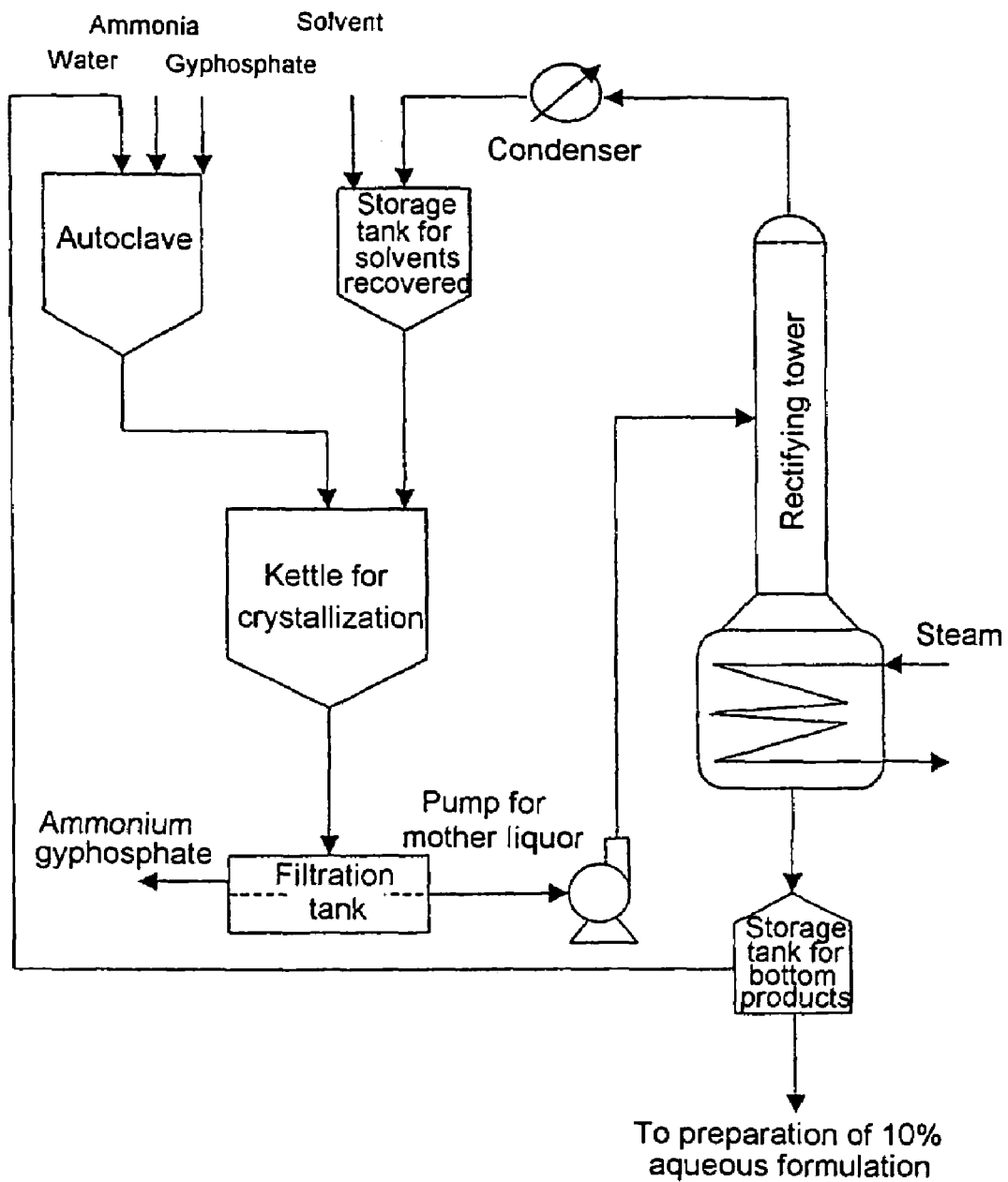
FIG. 1 is the schematic view of the process according to the present invention.
Figure 1:
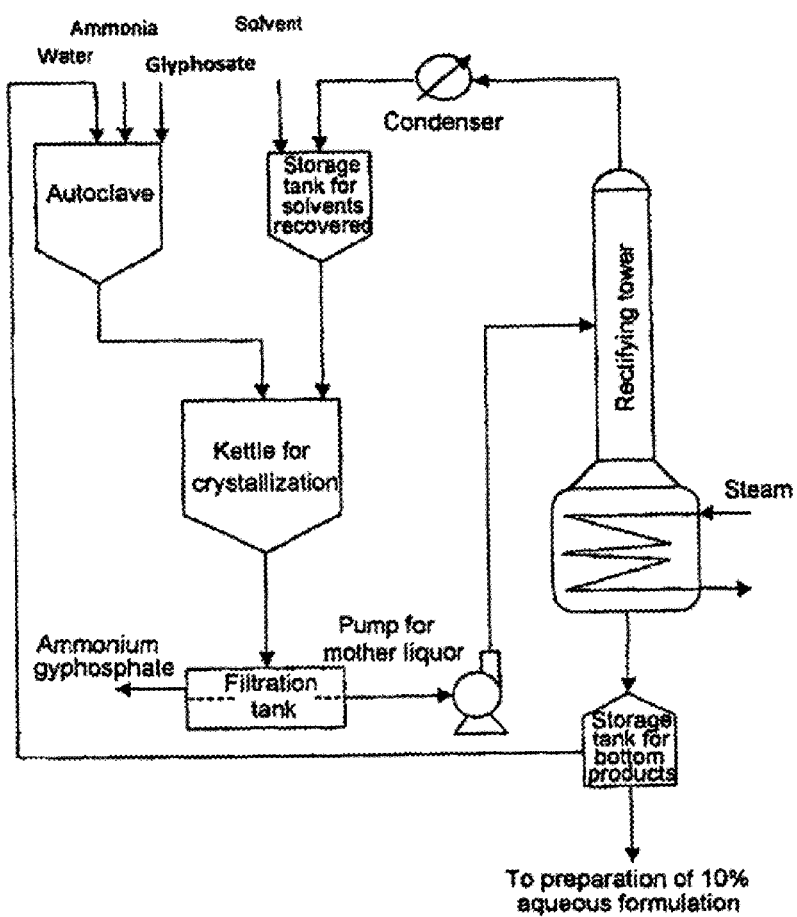

Methanol as an example is used to describe specifically the present invention. The present invention can be carried out with ethanol, methylal and other solvents that are suitable for the requirement of the process in a manner similar to methanol. The invention is intended to cover various modification that the solvents not listed in the present invention are used and that the operation parameters of the process are adjusted.

The embodiment according to the present invention is to obtain solid ammonium glyphosate by adding an appropriate amount of water to an autoclave equipped with a stirrer; adding once or in portions a crude glyphosate powder in an amount 0.2-2 times as that of the water by weight, wherein the crude glyphosate powder may be a 95% or more than 90% solid glyphosate that has been dried, or an undried glyphosate having 5-20% water content; then stirring for 5-30 minutes; subsequently introducing gaseous ammonia at a controlled temperature 30-100° C. to carry out the reaction for 0.5-3 hrs; stop inletting ammonia when the solution becomes clear and transparent; cooling the reaction solution to less than 30° C.; and then filtering.

The amount of gaseous ammonia introduced is 1.01-1.5 times by mole as that of glyphosate added. When the ammonia is not enough, the reaction will not be carried out completely to cause the product having relatively more glyphosate, and thus a part of the water-soluble solid ammonium glyphosate may not be dissolved due to very low the solubility of glyphosate in water. If the ammonia is introduced in excess, relatively more free ammonia will remain in the system, thereby the ammonia will escape in subsequent processes to result in the environmental pollution. A relatively simple method for judging the end point of the reaction is to measure the pH of the reaction system. The inventor believes that the pH should be kept at 5-8. The solubility of ammonium glyphosate varies with the concentration of the aqueous methanol solution, the higher the concentration of aqueous methanol solution is, the lower the solubility of ammonium glyphosate is. The saturation concentrations of ammonium glyphosate in different concentrations of the aqueous methanol solution at 30° C. are listed in Table 1.

TABLE 1

The saturation concentrations of ammonium glyphosate in different aqueous methanol solutions.

| | Content of methanol (w/w) % | | | | | |
|---|---|---|---|---|---|---|
| | 5 | 20 | 40 | 60 | 80 | 100 |
| Saturation concentration (w/w) % | 18.2 | 8.9 | 4.3 | 1.5 | 0.9 | 0.6 |

Although the solubility of ammonium glyphosate is lower in the higher concentration of aqueous methanol solution, when methanol is added too much (e.g. the ratio of methanol to water is higher than 10:1) and the amount of mother liquor is thus increased too high, on the contrary, the total amount of ammonium glyphosate dissolved in the mother liquor is increased and the utilization of the equipment is decreased.

The methanol used in the process can be recovered for reuse. After filtered, the mother liquor containing methanol, water, ammonium glyphosate, free ammonia, glyphosate and impurities is rectified to recover the methanol which is used for the crystallization and separation. After recovering methanol, the bottom residue containing 2-8% of the ammonium glyphosate may be returned to the synthesis process for the preparation of ammonium glyphosate, or used for the preparation of aqueous formulation of ammonium glyphosate by increasing the content of ammonium glyphosate therein and adding surfactants.

In the process according to the present invention, since the formation of nitrosamine which content needs to be controlled is substantially reduced due to reducing significantly the heat load for oven-drying, sodium sulfite as an antioxidant is not necessarily added during the whole reaction.

There is not particular limit to the methanol used for the crystallization and separation in the present invention, which may be industrial grade methanol of 98% by weight or recovered methanol of 90% by weight. So in the recovery process of methanol according to the present invention a simple distillation plant may be used without consumption of a great amount of steam to obtain a high content of methanol. In the present invention system, the mole ratio of methanol to water is 1-10:1, and preferred is 2-5:1.

The ammonium glyphosate salt obtained according to the process of the present invention can be directly used for preparing the solid formulation of ammonium glyphosate salt because of lower water content, and also can be dried in various manners such as pneumatic drying or oven-drying and the like without any agglomerate. The water content or organic solvent content in the ammonium glyphosate salt can be reduced to 0.1 -2% by oven drying.

The process for preparing the solid ammonium glyphosate salt according to the present invention is simple in methodology and low in cost, and the product has crystalline powder appearance after drying and is easily to be made into the water-soluble solid formulation.

All the raw materials, aids and additives used in the present invention are available from market.

The present invention is further illustrated by following specific examples that are only used to illustrate the present invention, but not limit the scope of the present invention. Unless otherwise specified, all the quantities, parts or percentages in the present invention are expressed by weight.

Specific Modes for Practicing the Invention

EXAMPLE 1

100 g of water and 120 g of the crude glyphosate powder (with a purity of 95%) were added once into a 2 L autoclave equipped with a stirrer and a thermometer. Ammonia was introduced in molar quantities 1.01 times as that of the net glyphosate used in the autoclave under stirring to carry out the reaction. The reaction temperature was controlled at 35±5° C. When the pH reached 5 as an end point after the reaction lasted for 3 hrs, the introduction of ammonia was ceased, and then the aqueous ammonium glyphosate solution was cooled to the temperature of 25±5° C. under stirring. 100 g of methanol was then added for the crystallization. The resulting crystals were filtered in suction from the system, and then dried to obtain the product of ammonium glyphosate.

EXAMPLE 2

The experiment process and equipment were the same as those in Example 1. Ammonia was introduced in molar quantities 1.2 times as that of the net glyphosate used under stirring to carry out the reaction, The reaction temperature was controlled at 70±5° C. When the pH reached 6.5 as an end point after the reaction lasted for 2 hrs, the introduction of ammonia was ceased. The aqueous ammonium glyphosate solution was cooled to the temperature of 25±5° C. under stirring. After the reaction, 225 g of methanol was added for the crystallization, and the resulting crystals were filtered in suction from the system, and then dried to obtain the product of ammonium glyphosate.

EXAMPLE 3

The experiment process and equipment were the same as those in Example 1. Ammonia was introduced in molar quantities 1.5 times as that of the net glyphosate used under stirring to carry out the reaction, The reaction temperature was controlled at 95±5° C. When the pH reached 6.5 as an end point after the reaction lasted for 1 hr, the introduction of ammonia was ceased. The aqueous ammonium glyphosate solution was cooled to the temperature of 25±5° C. under stirring. After the reaction, 450 g of methanol was added for the crystallization, and the resulting crystals were filtered in suction from the system and then dried to obtain the product of ammonium glyphosate.

EXAMPLE 4

The experiment process, equipment and reaction conditions were the same as those in Example 2, except that 675 g of methanol was added for the crystallization after the reaction.

EXAMPLE 5

The experiment process, equipment and reaction conditions were the same as those in Example 2, except that 900 g of methanol was added for the crystallization after the reaction.

EXAMPLE 6

The experiment process, equipment and reaction conditions were the same as those in Example 2, except that 1000 g of methanol was added for the crystallization after the reaction.

EXAMPLE 7

The experiment process, equipment and reaction conditions were the same as those in Example 3, except that 450 g of ethanol was added after the reaction.

EXAMPLE 8

The experiment process, equipment and reaction conditions were the same as those in Example 3, except that 450 g of methylal was added after the reaction.

EXAMPLE 9

The experiment process, equipment and reaction conditions were the same as those in Example 3, except that the solvent (450 g) used for the crystallization was consisted of methanol (65% by weight), methylal (25% by weight) and water (10% by weight).

EXAMPLE 10

The mother liquors obtained from Examples 1-6 by filtering were distilled to obtain the methanol (A) having a 95 wt % of content and the aqueous solution (B) containing 5.1 wt % of ammonium glyphosate, respectively. The process of Example 1 was carried out with 100 g of the wet glyphosate powder (8% of water content) and 100 g of B, except that 400 g A was added as the solvent.

EXAMPLE 11

The experiment process, equipment and reaction conditions were the same as those in Example 9, except that 450 g solvent (consisting of 50% methanol and 50% ethanol) was used for the crystallization.

EXAMPLE 12

The experiment process, equipment and reaction conditions were the same as those in Example 9, except that the solvent used for the crystallization was 450 g of n-propanol.

EXAMPLE 13

The experiment process, equipment and reaction conditions were the same as those in Example 9, except that the solvent used for the crystallization was 450 g of n-butanol.

EXAMPLE 14

The experiment process, equipment and reaction conditions were the same as those in Example 9, except that 550 g solvent (consisting of 50% methanol, 30% ethanol, 10% isopropanol and 10% tert-butanol) was used for the crystallization.

EXAMPLE 15

The experiment process, equipment and reaction conditions were the same as those in Example 9, except that 450 g solvent (consisting of 30% methanol, 50% ethanol, 20% methylal) was used for the crystallization.

EXAMPLE 16

The experiment process, equipment and reaction conditions were the same as those in Example 3, except that 680 g of ethanol was added after the reaction.

EXAMPLE 17

The experiment process, equipment and reaction conditions were the same as those in Example 2, except that 750 g of methylal was added after the reaction.

EXAMPLE 18

The experiment process, equipment and reaction conditions were the same as those in Example 9, except that the solvent used for the crystallization was 350 g of n-propanol.

EXAMPLE 19

The experiment process, equipment and reaction conditions were the same as those in Example 9, except that the solvent used for the crystallization was 400 g of n-butanol.

EXAMPLE 20

6.4 g of ammonium glyphosate was added to 100 g of II (containing 5.1% of ammonium glyphosate), then 8 g of EF8108 (produced by the Research Institute of Jinling Petrochemical Corporation of SINOPEC) was further added after dissolved under stirring. The resulting mixture was then mixed homogeneously to obtain a clear and transparent product having the same drug effect as that of aqueous formulation of 10% glyphosate available from market.

The purity and yield of product in each Example mentioned above are shown in Table 2 below, wherein the yields are calculated on the basis of the 95 wt % of glyphosate.

| Example | gyphosphate ammonium (%) | Yield (%) |
|---|---|---|
| 1 | 96.9 | 92.8 |
| 2 | 96.4 | 95.5 |
| 3 | 95.9 | 97.8 |
| 4 | 95.7 | 98.0 |
| 5 | 95.8 | 98.0 |
| 6 | 96.0 | 97.3 |
| 7 | 95.8 | 98.5 |
| 8 | 95.2 | 98.7 |
| 9 | 95.7 | 98.1 |
| 10 | 95.1 | 98.8 |
| 11 | 96.0 | 98.3 |
| 12 | 96.2 | 95.1 |
| 13 | 96.4 | 94.2 |
| 14 | 96.1 | 96.4 |
| 15 | 95.8 | 94.7 |
| 16 | 96.3 | 95.2 |
| 17 | 95.8 | 96.8 |
| 18 | 95.6 | 94.8 |
| 19 | 96.2 | 96.7 |

The invention claimed is:

1. A process for preparing solid ammonium glyphosate by extraction with an organic solvent, which comprises adding glyphosate and water without addition of an organic solvent into a normal reactor, introducing gaseous ammonia for the reaction to obtain an aqueous ammonium glyphosate solution after the reaction is completed, characterized in that, after the reaction is completed, an organic solvent is added into the reaction solution, wherein said organic solvent has a relatively high solubility in water or is miscible with water in any proportion, and the solid ammonium glyphosate is obtained by crystallizing and filtering in suction.

2. The process according to claim 1 wherein said organic solvent comprises an acetal, a monobasic alcohol having 1-4 carbon atoms, or a mixture thereof.

3. The process according to claim 2 wherein said organic solvent comprises an acetal, or a monobasic alcohol having 1-4 carbon atoms.

4. The process according to claim 2 or 3 wherein said monobasic alcohol having 1-4 carbon atoms comprises methanol, ethanol propanol or n-butanol, and said acetal comprises methylal.

5. The process according to claim 1 wherein the added organic solvent to water content in the reaction solution has a weight ratio of 1:1-10:1.

6. The process according to claim 1 wherein the added organic solvent to water content in the reaction solution has a weight ratio of 2:1-5:1.

7. The process according to claim 1 wherein said glyphosate is an undried powder having a water content of 5-20%, or a dry powder having a glyphosate content more than 90% by weight, and the glyphosate to water added in the reactor has a weight ratio of 0.2-2:1.

8. The process according to claim 1 wherein the ammonia to the glyphosate added to the reactor has a mole ratio of 1.01:1-1.5:1.

9. The process according to claim 1 wherein the reaction is carried out under a temperature of 30-100° C. and at the completion of the reaction, the reaction solution has a pH of 5-8.

10. The process according to claim 1 wherein the solid ammonium glyphosate obtained from filtration is further dried to make the water and organic solvent contained therein decreased to less than 0.1-2%.

11. The process according to claim 1 wherein a mother liquor is collected after the filtration which contains the organic solvent, is separated by rectification or distillation, and the organic solvent is returned for use in the crystallization, and the aqueous solution containing ammonium glyphosate is returned back to the reaction process.

12. The process according to claim 1 wherein the aqueous solution containing ammonium glyphosate is used for preparing the aqueous formulation of ammonium glyphosate salt.

* * * * *

UNITED STATES PATENT AND TRADEMARK OFFICE
CERTIFICATE OF CORRECTION

PATENT NO. : 7,435,847 B2
APPLICATION NO. : 10/521649
DATED : October 14, 2008
INVENTOR(S) : Wei Wang et al.

It is certified that error appears in the above-identified patent and that said Letters Patent is hereby corrected as shown below:

Title Page:

Inventors:

"(75) Jiang Li, Jiande (TW)" should read -- (75) Jiang Li, Jiande (CN) --

Title Page:

"Assignee: Zhejiang Xin', Zhejiang Province (CN)"

should read

-- Assignee: Zhejiang Xin'an Chemical Industrial Group Co. Ltd., Zhejiang Province (CN) --

Figure 1:

Delete Drawing Figure 1, and Repalce with Drawing Figure 1. (Attached)

Signed and Sealed this

Tenth Day of March, 2009

JOHN DOLL
*Acting Director of the United States Patent and Trademark Office*